(12) United States Patent
Meulink

(10) Patent No.: US 8,790,413 B2
(45) Date of Patent: Jul. 29, 2014

(54) ORTHOPAEDIC IMPLANT SLEEVE AND METHOD

(75) Inventor: Steven L. Meulink, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 1729 days.

(21) Appl. No.: 11/259,905

(22) Filed: Oct. 27, 2005

(65) Prior Publication Data

US 2007/0100464 A1   May 3, 2007

(51) Int. Cl.
*A61F 2/30* (2006.01)
*A61F 2/00* (2006.01)
*A61F 2/36* (2006.01)
*A61F 2/46* (2006.01)

(52) U.S. Cl.
CPC ..... *A61F 2/3609* (2013.01); *A61F 2002/30718* (2013.01); *A61F 2002/30332* (2013.01); *A61F 2002/3625* (2013.01); *A61F 2002/4635* (2013.01); *A61F 2/0095* (2013.01); *A61F 2002/30341* (2013.01); *A61F 2002/3652* (2013.01); *A61F 2002/30604* (2013.01); *A61F 2002/3082* (2013.01); *A61F 2220/0033* (2013.01); *A61F 2002/30235* (2013.01); *A61F 2002/30616* (2013.01); *A61F 2230/0069* (2013.01); *A61F 2002/365* (2013.01); *A61F 2002/3611* (2013.01); *A61F 2/367* (2013.01); *A61F 2002/30334* (2013.01); *A61F 2002/3631* (2013.01)
USPC ..................................... 623/23.46

(58) Field of Classification Search
USPC ......... 623/22.12, 22.46, 22.33, 23.23, 23.52; 607/171, 172; 606/76, 176; 604/171; 206/438, 363–370
See application file for complete search history.

(56) References Cited

U.S. PATENT DOCUMENTS

| | | | |
|---|---|---|---|
| 4,064,567 A | | 12/1977 | Burstein |
| 4,113,088 A | * | 9/1978 | Binkhorst ............ 206/210 |
| 4,726,359 A | | 2/1988 | Schroeder |
| 4,728,335 A | | 3/1988 | Jurgutis |
| 4,921,500 A | | 5/1990 | Averill |
| 5,035,717 A | | 7/1991 | Brooks |
| 5,080,679 A | | 1/1992 | Pratt et al. |
| 5,108,452 A | | 4/1992 | Fallin |
| 5,116,379 A | | 5/1992 | McLardy-Smith |
| 5,156,624 A | | 10/1992 | Barnes |
| 5,156,626 A | | 10/1992 | Broderick et al. |
| 5,308,673 A | | 5/1994 | Tochacek |
| 5,362,311 A | | 11/1994 | Amino et al. |
| 5,580,352 A | | 12/1996 | Sekel |
| 5,626,605 A | * | 5/1997 | Irie et al. ............... 623/1.1 |
| 5,755,800 A | | 5/1998 | O'Neil et al. |
| 5,858,020 A | | 1/1999 | Johnson et al. |
| 5,906,644 A | | 5/1999 | Powell |

(Continued)

FOREIGN PATENT DOCUMENTS

| | | |
|---|---|---|
| DE | 3609120 A1 | 9/1987 |
| EP | 0634154 A1 | 1/1995 |
| WO | WO98/08468 A1 | 3/1998 |
| WO | WO02/07653 A1 | 1/2002 |

*Primary Examiner* — David Isabella
*Assistant Examiner* — Ann Schillinger
(74) *Attorney, Agent, or Firm* — Schwegman Lundberg & Woessner, P.A.

(57) ABSTRACT

A protective sleeve is provided that is useful during minimally invasive surgery to facilitate assembly of modular components. The sleeve prevents contamination of a second component as it is engaged with a previously inserted component. The sleeve may also serve to guide insertion of the second component to facilitate aligning it with the previously inserted component.

19 Claims, 3 Drawing Sheets

(56) References Cited

U.S. PATENT DOCUMENTS

| | | |
|---|---|---|
| 6,090,146 A | 7/2000 | Rozow, III et al. |
| 6,238,435 B1 | 5/2001 | Meulink et al. |
| 6,287,291 B1 | 9/2001 | Bigus |
| 6,330,845 B1 | 12/2001 | Meulink |
| 6,428,578 B2 | 8/2002 | White |
| 6,432,141 B1 * | 8/2002 | Stocks et al. ............... 623/22.13 |
| 6,607,560 B1 | 8/2003 | Pfaff et al. |
| 6,663,670 B2 | 12/2003 | Rogers et al. |
| 6,682,566 B2 | 1/2004 | Draenert |
| 6,692,530 B2 | 2/2004 | Doubler et al. |
| 6,802,866 B2 | 10/2004 | Bunz |
| 6,863,692 B2 * | 3/2005 | Meulink ..................... 623/23.52 |
| 6,875,239 B2 | 4/2005 | Gerbec et al. |
| 2002/0116068 A1 | 8/2002 | McLean |
| 2003/0074078 A1 | 4/2003 | Doubler et al. |
| 2004/0122525 A1 | 6/2004 | Daniels et al. |
| 2005/0004679 A1 | 1/2005 | Sederholm et al. |
| 2005/0143828 A1 * | 6/2005 | Collins et al. ............. 623/18.11 |

* cited by examiner

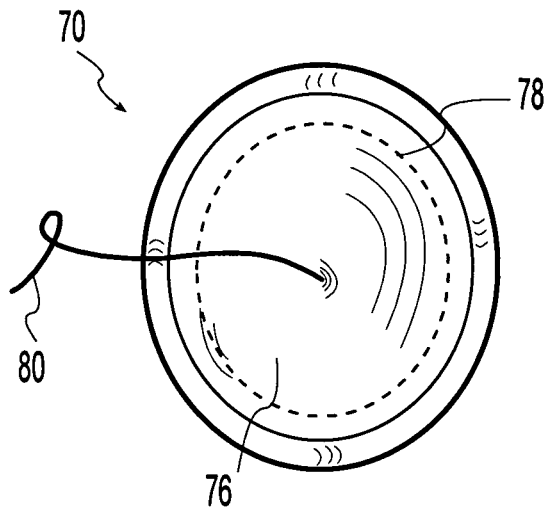
*Fig. 3*
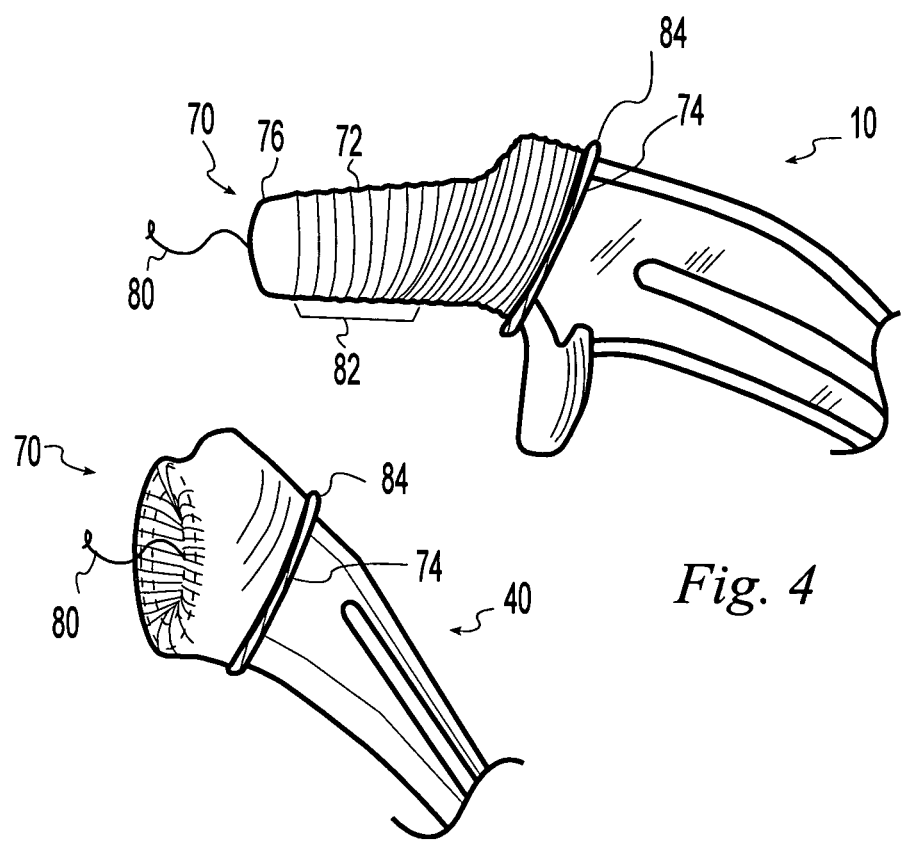
*Fig. 4*
*Fig. 5*

ORTHOPAEDIC IMPLANT SLEEVE AND METHOD

FIELD OF THE INVENTION

The present invention relates to devices for protecting medical implant components during implantation of the components into a surgical wound. In particular, the present invention relates to a protective sleeve useful during minimally invasive surgery to facilitate in vivo assembly of modular components.

BACKGROUND

Medical implants to replace or augment various parts of the mammalian body have been successfully used to reduce pain and improve function. For example, orthopaedic implants for replacing portions of bones and joints damaged by disease and/or trauma often eliminate pain and/or increase mobility. Orthopaedic implants for hips, knees, shoulders, ankles, elbows, wrists, the digits of the hands and feet, vertebral bodies, spinal discs, and other bones and joints have been developed. Many medical implants are made more versatile by providing them as separate modular components that can be combined to form an implant suited to a particular patient's condition. Where such modular components are supplied, a means for attaching them to one another is provided.

Increasingly, surgeons are turning to minimally invasive surgical techniques in which a surgical procedure is performed through small incisions to minimize trauma to surrounding tissues and speed patient recovery. One difficulty arising from the use of minimally invasive surgery with modular components is avoiding contamination of the junction between the components. In the process of inserting modular components through small incisions, body fluids and tissues are easily deposited on the junction surfaces. Such deposits may cause the junction to be less secure. Therefore, the surgeon often must carefully clean and dry the junction after inserting the components. This may be difficult or impossible depending on the shape and location of the junction and the size and orientation of the surgical incision. U.S. Pat. No. 6,863,692 issued Mar. 8, 2005, to the present inventor and addresses solutions to this problem. In the '692 patent a removable sleeve protects a modular junction of an implant and/or an anchoring portion of the implant. In one embodiment, a sleeve wipes a junction clean after insertion of implant components into a surgical site. In another embodiment, a sleeve covers a portion of an implant during insertion through the surgical wound and is then removed from the implant. In another embodiment, a sleeve covers a portion of an implant and is simultaneously withdrawn from the implant as the portion is seated in the surgical site such as into contact with a bone or into contact with cement.

Another difficulty arising from the use of minimally invasive surgery with modular components is aligning a second component with a previously inserted component so that they can be assembled. Minimally invasive incisions can be difficult to see into. Furthermore, such incisions can be deep and even convoluted. Therefore, upon insertion of a second component to be engaged with a previously inserted component, the surgeon may have to manipulate the joint position and/or the second component within the wound to get the components to engage. Such feeling around can prolong the surgical procedure, lead to contamination of the junction, and lead to poor alignment of the components.

SUMMARY

The present invention provides a protective sleeve useful during minimally invasive surgery to facilitate assembly of modular components In one aspect of the invention, a sleeve for use with a modular orthopaedic implant includes a first end, a second end, and a flexible sidewall defining an enclosed passageway extending from the first end to the second end. The first end is engageable with a first implant component such that the sleeve surrounds a first portion of a modular junction. The second end of the sleeve extends from the first end such that a second implant component may be passed along the passageway to engage the first implant component.

In another aspect of the invention, a sleeve and implant combination includes a first implant component having a first engaging portion of a junction, a second implant component having a second engaging portion of a junction, and a sleeve removably mounted on the first component. The sleeve is extendable from a first position in which it is stowed on the first implant component surrounding a portion of the first engaging portion to a second position in which the sleeve defines an elongated protective passageway extending away from the first implant component such that the second implant component may be passed along the passageway to engage the first implant component.

In another aspect of the invention, a method includes: attaching a first end of a sleeve to a first modular implant component; inserting the first modular implant component into the surgical site; and passing the second modular implant component through the sleeve from a second end to the first end to engage the first modular implant component.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 3 is a top plan view of an illustrative sleeve according to the present invention rolled into a compact configuration;

FIG. 4 is a perspective view of the sleeve of FIG. 3 placed on the implant of FIG. 1;

FIG. 5 is a perspective view of the sleeve of FIG. 3 placed on the implant of FIG. 2;

DESCRIPTION OF THE ILLUSTRATIVE EXAMPLES

Figure 1:
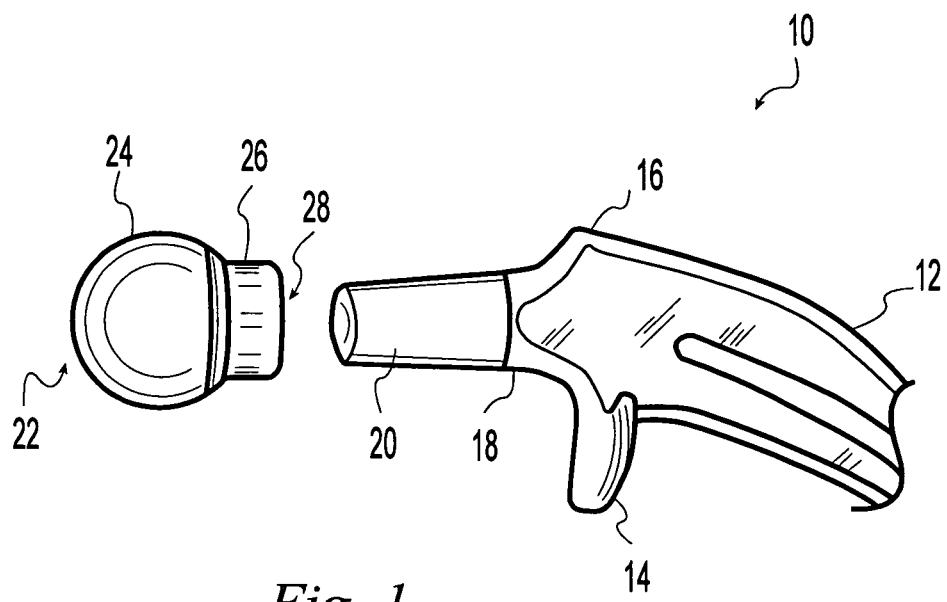
FIG. 1 is a perspective view of a modular implant having two components forming a male/female junction, the first-inserted component having a male portion of the junction, with which the sleeve of the present invention may be used.

Embodiments of an orthopaedic implant sleeve include a flexible sleeve positionable over a portion of an implant and extendable from the implant to form a passageway leading to the implant. The sleeve may be in the form of an open ended flexible tube. Alternatively, one or both ends of the sleeve may be closed initially and opened by the user as needed. A closed end may be frangible so that it can be torn by finger pressure alone. A closed end may be severable with a cutting instrument such as a blade or scissors. A closed end may be scored, perforated, embossed, or otherwise configured to ease opening of the end.

The sleeve may be rolled into a compact disc configuration prior to use to facilitate rolling it onto an implant component. In use, the sleeve may be unrolled to a desired length and then a portion of the sleeve may be rolled onto the implant component. The sleeve may be bunched or pleated to facilitate stowing it on the implant component prior to unfurling it in use. The sleeve may be provided to the end user pre-applied to the implant component or the sleeve may be provided separately and applied by the end user. The sleeve may extend from the implant component prior to insertion of the implant component into the surgical wound or it may be extended after insertion of the implant component. The sleeve may include a pull cord to facilitate grasping the sleeve and deploying it in use. The cord may be sized to extend from the surgical wound prior to deploying the sleeve so that there is no need to reach into the wound to grasp the cord or sleeve.

The sleeve may be elastic, with relatively high stretchability, or it may be inelastic, with relatively low stretchability. An elastic sleeve may be sized so that it stretches to conform closely to the shape of the implant and to aid in gripping the implant. An elastic sleeve may be stretched beyond its at rest physical dimensions to allow it to extend in a stretched configuration through wounds of varying lengths. An elastic sleeve may also be stretched transversely to allow passage of oversized components along the sleeve passageway. An inelastic sleeve may facilitate forming a taut passageway along which a second component may be easily guided. Examples of suitable flexible materials, both elastic and inelastic, include polyurethane, polyethylene, polyesters, polyolefins, polyimides, polyamides, polyacrylates, poly(ketones), fluropolymers, natural rubber, synthetic rubber, aluminum, titanium, steel, and/or other suitable materials, alloys, and combinations. These materials may be in the form of sheets, films, woven fabrics, non-woven fabrics, foils, laminates, and/or other suitable forms and combinations of forms. For example, the sleeve may be advantageously made from a polymer film. Such a film may for example include any one of or combination of polyethylene, polyurethane, and/or natural or synthetic rubber.

The sleeve may include a base ring of material at one end that tightly grips the implant to maintain its position on the implant until complete removal is desired. The base ring may be formed by rolling the sleeve, molding, and/or incorporating a separate ring shaped component. The base ring may be elastic such that it stretches to grip the implant component.

The sleeve may include a member to maintain an opening outside of the wound. For example, an opening ring may be incorporated into one end of the sleeve. Such an opening ring may be elastic to allow it to be compressed during passage through the wound yet be self-biased into an open configuration outside of the wound. An opening ring may also be inelastic to form a rigid opening for the sleeve. An opening ring may be formed as a permanent part of the sleeve such as by rolling the sleeve, molding, and/or incorporating a separate ring shaped component. An opening ring may also be provided as a separate element applied to the sleeve opening during use to maintain the sleeve adjacent the exterior of the wound in an open position. For example, a rigid tube, ring, clip, and/or other component may be applied to the sleeve opening after the sleeve is unfurled. Furthermore, the sleeve opening may be maintained in use by way of conventional retractors as are known in the art.

Figure 2:
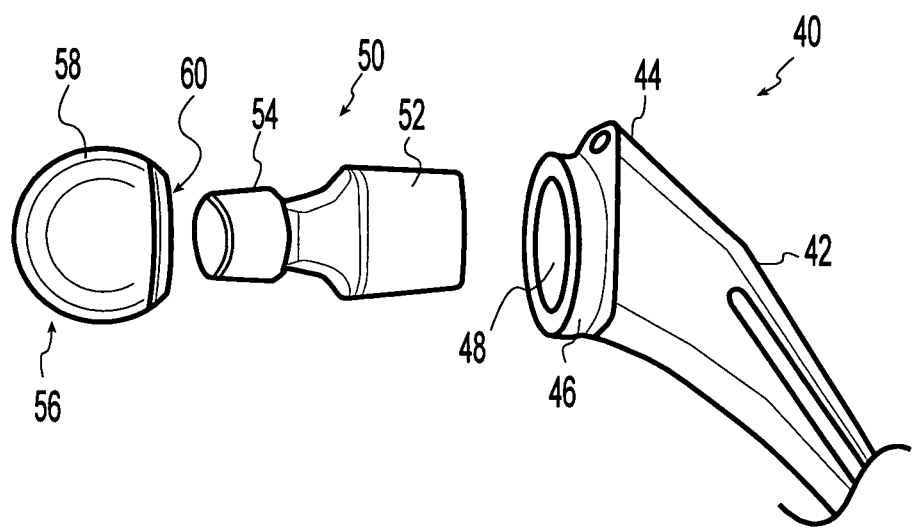
FIG. 2 is a perspective view of a modular implant having three components forming two male/female junctions, the first-inserted component having a female portion of a junction, with which the sleeve of the present invention may be used.

FIGS. 1 and 2 depict exemplary modular implants with which the sleeve of the present invention may be used. While FIGS. 1 and 2 depict hip stem implants with male/female modular junctions, it is contemplated that the sleeve of the present invention may be used with modular implants for hips, knees, shoulders, ankles, elbows, wrists, the digits of the hands and feet, vertebral bodies, spinal discs, and other bones and joints with any suitable way of connecting the modular components.

FIG. 1 depicts an implant 10 having a stem 12 for insertion into a first bone to anchor the implant 10. A collar 14 rests on the bone to further support and stabilize the implant 10. A shoulder 16 defines the upper region of the stem 12 and a neck 18 extends from the shoulder and defines a male taper forming a male portion 20 of a male/female modular implant junction. A separate ball head 22 includes an articular portion 24 for articulation with an opposing second bone. The head 22 includes a skirt 26 defining an internal bore or female portion 28 of the male/female modular implant junction. In the example, the male and female portions 20, 28 form complimentary self-locking Morse tapers. In use, the needed implant is assembled by combining a suitably sized head 22 with a suitably sized stem 12. The head 22 is placed on the neck 18 and impacted to lock the components together.

FIG. 2 depicts an implant 40 having a stem 42 for insertion into a first bone to anchor the implant 40. A shoulder 44 defines the upper region of the stem 42 and a short spigot 46 extends from the shoulder 44 and defines an internal bore or female portion 48 of a male/female modular implant junction. A separate neck component 50 has a double-ended configuration with a stem-engaging taper 52 on one end and a head engaging taper 54 at the other end. A separate ball head 56 includes an articular portion 58 and a female junction 60. In the example, the stem/neck junction is in the form of an oblong taper and the head/neck junction is in the form of a Morse taper. The implant of FIG. 2 is advantageously adaptable because it allows independent selection of head, neck, and stem configurations. Furthermore, the implant 40 of FIG. 2 is particularly well suited to minimally invasive surgery since without a protruding collar or neck the stem 42 is easily manipulated through a narrow incision. After the stem 42 is inserted, the neck 50 and head 56 may easily be passed through a narrow incision to be joined with the stem 42.

FIGS. 3-7 depict an exemplary sleeve 70. The sleeve 70 is a tube having a sidewall 72, a first end 74, and a second end 76. The exemplary sleeve 70 is formed from a thin polymer film. The first end 74 is open to engage the implant and the second end is optionally open or closed. The exemplary sleeve has a closed end 76. FIG. 3 shows the sleeve 70 rolled into a compact configuration prior to being applied to an implant component. A closed second end 76 may optionally include a scored, embossed, and/or perforated portion 78 to facilitate opening the second end 76 in use such as by cutting or tearing.

An optional pull cord 80 is attached to the second end 76 to facilitate deploying the sleeve 70. The pull cord 80 may be attached at any convenient location adjacent the second end 76. For example, the pull cord 80 may be attached to the center of the second end 76 as shown. In another example, if the second end 76 is open, the pull cord 80 may be attached to the edge of the opening. Alternatively, the pull cord 80 may be tied around an open second end 76 to close it. The pull cord 80 is advantageously sized so that it reaches from the exterior of the wound to the sleeve 70 while the sleeve is not yet deployed and the implant is seated at the surgical site. In this way one end of the pull cord can remain outside of the wound while the implant and sleeve are inserted. The pull cord 80 can then be grasped and pulled to extend the sleeve.

FIG. 4 shows the sleeve 70 positioned over a male portion of a male/female junction. If the sleeve 70 is first rolled as in FIG. 3, it may be unrolled to a desired length and then a portion of the sleeve 70 may be unrolled over the end of the implant 10 to cover the junction and protect it from contamination during insertion. Alternatively, the sleeve can be provided in a loose, unrolled configuration and pulled over the implant 70 like a sock. Extra material may be bunched or gathered into folds 82 on the implant 10. The sleeve 70 may include pleats formed by molding, scoring, or otherwise formed to cause it to collapse into a folded state on the implant 10. A base ring 84 grips the implant 10 and holds the sleeve 70 in place.

FIG. 5 shows the sleeve 70 positioned over a female portion of a male/female junction. In this example, extra material is tucked into the female opening as shown. The pull cord 80 extends from the opening to ease deploying the sleeve 70.

In use (FIGS. 6 and 7), the sleeve 70 is placed on a first implant component 40 to cover a portion of a junction. The first implant component 40 is then inserted through a surgical incision until it is seated in the desired location at the surgical site. The sleeve protects the portion of the junction on the first implant component 40 from contamination during insertion. The sleeve 70 is then unfurled from the first implant component 40 by pulling the second end away from the component 40. Where the optional pull cord 80 is included, it is grasped and pulled to unfurl the sleeve 70. Where the optional base ring 84 is included, it helps to keep the sleeve in contact with the first implant component 40. Where the second end 76 is closed, it may now be opened by cutting, tearing, and/or otherwise parting the closed end. When unfurled, the sleeve 70 defines a protected passageway from the first implant component 40 to the exterior of the surgical wound to provide uncontaminated passage for a second implant component 50. The opening at the second end 76 may be maintained by the user such as by gripping the edges of the opening with the user's fingers. Optionally, the opening may be maintained with surgical retractors inserted into the opening to pull and hold the edges in an open configuration. The exemplary sleeve 70 shown in FIG. 7 includes an opening ring 86 incorporated into the second end 76 to maintain the opening in an open state.

Figure 6:
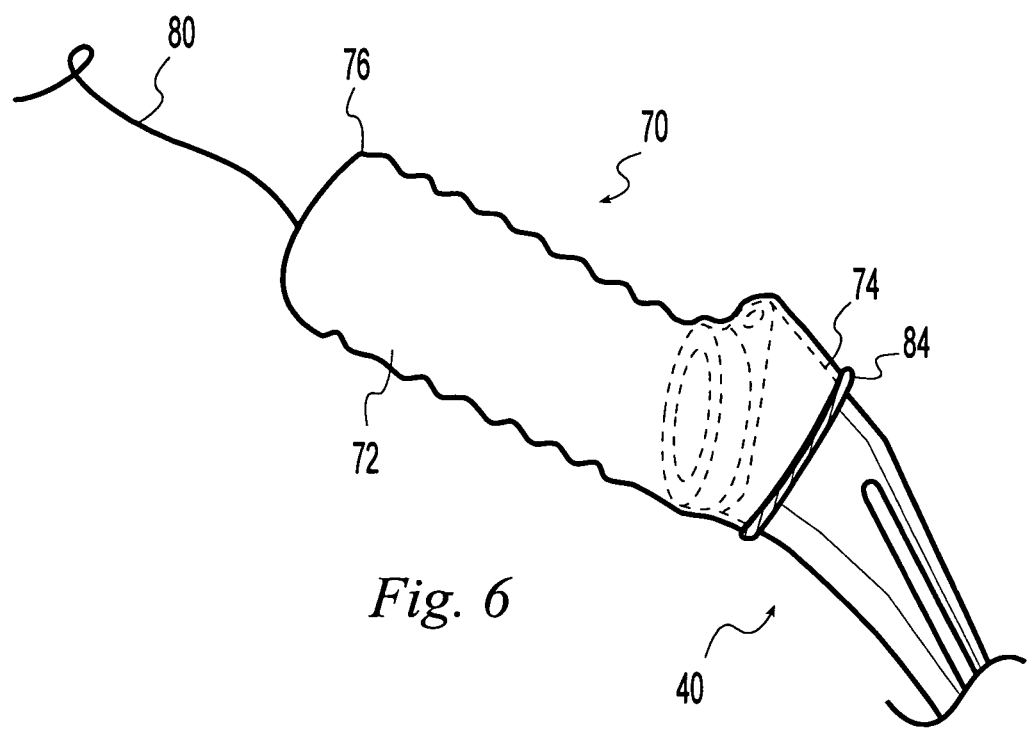
FIG. 6 is a perspective view of the sleeve of FIG. 3 unfurled from the implant of FIG. 2 to form a passageway leading to the implant.
Figure 7:
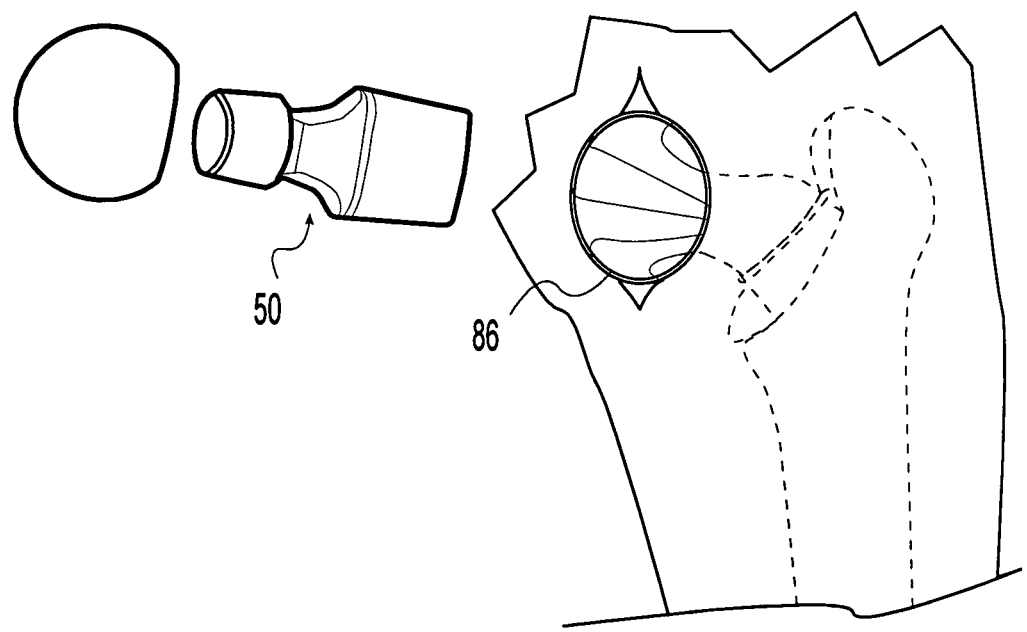
FIG. 7 is a perspective view showing the implant of FIG. 2 inserted into a bone and the sleeve of FIG. 3 unfurled to form a passageway from the implant to the exterior of a surgical wound.

Alternatively, the sleeve 70 may be extended from the first implant component as shown in FIG. 6 prior to insertion of the first implant component and the second end 76 of the sleeve 70 may remain outside of the surgical wound throughout the procedure.

The second implant component 50 is passed through the opening in the second end 76, along the passageway defined by the sleeve 70, and is joined to the first implant component 40 by engaging the junction within the protected environment of the sleeve 70. Where the surgical wound is narrow and/or convoluted, the sleeve 70 allows the second implant component 50 to be passed blindly along the passageway defined by the sleeve 70 to guide the second implant component 50 into engagement with the first component 40. Thus, the sleeve protects the portions of the junction from contamination during insertion, provides a protected environment for junction assembly, and serves to guide the components into engagement to facilitate blind assembly. The sleeve 70 may be removed from the surgical site by further pulling on the second end 76 and/or pull cord 80 to disengage the first end 74 from the first component 40.

Although examples of an orthopaedic implant sleeve and method have been described and illustrated in detail, it is to be understood that the same is intended by way of illustration and example only and is not to be taken by way of limitation. The invention has been illustrated in use to facilitate the insertion and assembly of a modular hip implant during total joint replacement surgery. However, the orthopaedic implant sleeve may be configured for use at other locations within a patient's body to insert and assemble other types of modular implants. Accordingly, variations in and modifications to the orthopaedic implant sleeve and its use will be apparent to those of ordinary skill in the art, and the following claims are intended to cover all such modifications and equivalents.

What is claimed is:

1. A sleeve and implant combination comprising:
a first implant component having an outer surface and a first engaging portion of a junction;
a second implant component separate from the first implant component and having a second engaging portion removably engageable with the first engaging portion of the junction;
a sleeve having a first end, a second end, and a sidewall extending from the first end to the second end, the first end of the sleeve removably mounted on the outer surface of the first implant component at a location spaced away from the first engaging portion, the sidewall of the sleeve surrounding at least a portion of the first engaging portion, the sleeve being extendable from a first position in which the sleeve is stowed on the first implant component with the sidewall surrounding at least a portion of the first engaging portion to a second position in which the sidewall of the sleeve defines an elongated protective passageway extending away from the location spaced away from the first engaging portion of the first implant component such that the second implant component may be passed through the passageway to engage the first implant component while the first end of the sleeve is removably mounted on the outer surface of the first implant component at the location spaced away from the first engaging portion, whereby, with the first engaging portion engaged with the second engaging portion, the sleeve may be disconnected from the first implant component, the sleeve having a closed configuration in which the second end of the sleeve is closed and an open configuration in which the second end of the sleeve is open, wherein the second end of the sleeve encloses the first engaging portion of the first implant component when the sleeve is in the closed configuration and receives the second implant component when the sleeve is in the open configuration.

2. The combination of claim 1 wherein the sleeve comprises a thin flexible polymer film.

3. The combination of claim 1 further comprising a pull cord connected to the second end and extendable away from the second end.

4. The combination of claim 1 wherein the first and second implant components comprise a modular hip joint prosthesis and define a male/female junction between them.

5. The combination of claim 1 wherein the second end of the sleeve is perforated to facilitate opening the second end of the sleeve in the open configuration.

6. The combination of claim 1, said sleeve further comprising a base ring at the first end, the base ring defining an opening and removably mounted on and surrounding the outer surface of the first implant component at a location spaced away from the first engaging portion of the first implant component.

7. The sleeve and implant combination of claim 1, further including an opening ring incorporated into the second end of the sleeve and configured to keep the second end open during use of the sleeve.

8. The sleeve and implant combination of claim 7, wherein the opening ring is formed as a permanent part of the sleeve.

9. The sleeve and implant combination of claim 7, wherein the opening ring is a separate element applied to the second end during use.

10. The sleeve and implant combination of claim 7, wherein the opening ring is inelastic and forms a rigid opening for the sleeve.

11. A sleeve and implant combination comprising:
a first implant component having an outer surface and a first engaging portion of a junction;
a second implant component separate from the first implant component and having a second engaging portion removably engageable with the first engaging portion of the junction; and
a sleeve having a first end, a second end, and a sidewall extending from the first end to the second end, the first end of the sleeve removably mounted on the outer surface of the first implant component at a location spaced away from the first engaging portion, the sidewall of the sleeve surrounding at least a portion of the first engaging portion, the sleeve being extendable from a first position in which the sleeve is stowed on the first implant component with the sidewall surrounding at least a portion of the first engaging portion to a second position in which the sidewall of the sleeve defines an elongated protective passageway extending away from the location spaced away from the first engaging portion of the first implant component such that the second implant component may be passed through the passageway to engage the first implant component while the first end of the sleeve is removably mounted on the outer surface of the first implant component at the location spaced away from the first engaging portion, whereby, with the first engaging portion engaged with the second engaging portion, the sleeve may be disconnected from the first implant component, the second end of the sleeve extending beyond the second implant component when the sleeve is in the second position and the first and second engaging portions of the first and second implant components are engaged, whereby, with the first and second implant components implanted inside a patient's body, the second end of the sleeve extends beyond the second implant component to a location outside of the patient's body.

12. The combination of claim 11 wherein the sidewall of the sleeve includes a plurality of folds that gather in the first position.

13. The combination of claim 12 wherein the plurality of folds spread apart in the second position.

14. The combination of claim 11, wherein the first engaging portion of the first implant component is a female cavity, the second end of the sleeve being tucked inside the female cavity in the first position.

15. The combination of claim 11, said sleeve further comprising a base ring at the first end, the base ring defining an opening and removably mounted on and surrounding the outer surface of the first implant component at a location spaced away from the first engaging portion of the first implant component.

16. The sleeve and implant combination of claim 11, further including an opening ring incorporated into the second end of the sleeve and configured to keep the second end open during use of the sleeve.

17. The sleeve and implant combination of claim 16, wherein the opening ring is formed as a permanent part of the sleeve.

18. The sleeve and implant combination of claim 16, wherein the opening ring is a separate element applied to the second end during use.

19. The sleeve and implant combination of claim 16, wherein the opening ring is inelastic and forms a rigid opening for the sleeve.

* * * * *